US006517476B1

(12) United States Patent
Bedoya et al.

(10) Patent No.: US 6,517,476 B1
(45) Date of Patent: Feb. 11, 2003

(54) CONNECTOR FOR IMPLANTABLE HEARING AID

(75) Inventors: Jose H. Bedoya, Boulder, CO (US); James Roy Easter, Lyons, CO (US); Richard Marshal DeMoss, Berthoud, CO (US)

(73) Assignee: Otologics LLC, Boulder, CO (US)

( * ) Notice: Subject to any disclaimer, the term of this patent is extended or adjusted under 35 U.S.C. 154(b) by 25 days.

(21) Appl. No.: 09/583,315

(22) Filed: May 30, 2000

(51) Int. Cl.[7] .............................................. H04R 25/00
(52) U.S. Cl. ........................................................ 600/25
(58) Field of Search ............................ 600/25; 439/668, 439/905; 607/2, 5, 36, 37, 38; 381/69

(56) References Cited

U.S. PATENT DOCUMENTS

| | | | |
|---|---|---|---|
| 3,764,748 A | 10/1973 | Branch et al. | 179/107 |
| 3,838,468 A | 10/1974 | Armstrong | 3/1 |
| 4,462,401 A | 7/1984 | Burgio | 128/303 |
| 4,462,402 A | 7/1984 | Burgio | 128/303 |
| 4,487,210 A | 12/1984 | Knudsen et al. | 128/785 |
| 4,498,461 A | 2/1985 | Hakansson | 128/1 |
| 4,516,820 A | 5/1985 | Kuzma | 339/48 |
| 4,606,329 A | 8/1986 | Hough | 128/1 |
| 4,612,915 A | 9/1986 | Hough et al. | 128/1 |
| 4,617,913 A | 10/1986 | Eddington | 128/1 |
| 4,628,907 A | 12/1986 | Epley | 128/1 |
| 4,655,776 A | 4/1987 | Lesinski | 325/10 |
| 4,756,312 A | 7/1988 | Epley | 128/420.5 |
| 4,774,933 A | 10/1988 | Hough et al. | 600/25 |

(List continued on next page.)

OTHER PUBLICATIONS

HNO Hals–Nasen–Ohren–Heilkunde, Kopf– und Hals–Chirurgie; Elektornicsche Horimplantate bei Innenohrschwerhorigkeiten; Springer; pp. A3–A5 and 737–880.

The University of Tubingen Course on Implantation of Sensory Endoprostheses for SNHL; Total Implanatation for TIC by Hans–Peter Zenner; pp. 1–32.

Implantation Methods for the Vibrant Soundbridge; Symphonix; pp. 1–16.

Vibrant Soundbridge System; Vibrating Ossicular Prosthesis; Symphonix; pp. 1–5.

Vibrant Soundbridge; Audio Processor D, Bringing Digital Sound to Life; Symphonix; pp. 1–5.

*Primary Examiner*—Max F. Hindenburg
*Assistant Examiner*—Brian Szmal
(74) *Attorney, Agent, or Firm*—Marsh Fischmann & Breyfogle LLP

(57) ABSTRACT

The present invention is directed to implantable hearing aid systems and provides for selective interconnection between two or more implantable components of a system. The inventive apparatus comprises a first connector interconnected to a first implantable component and a second connector interconnected to a second implantable component which is separate from the first implanted component. The first and second connectors may each comprise outer housings and internal conductors, wherein the outer housings are configured to define male and female connectors for mating interconnection therebetween. In one arrangement, a female connector is defined by a support structure that also supports an interconnected implantable component (e.g., a processor unit and/or induction coil), and wherein the male connector is interconnected to another, separate component (e.g., a middle ear actuator). The support structure may be integrally defined by a molded material (e.g., a silicon-based material). One or more locking member(s) may be provided for selective insertion into the outer housing of the female connector to securably engage the male connector (e.g., the central conductor thereof). The invention facilitates in situ interconnection of plural implantable components in an implantable hearing aid system, and further allows for selective removal/repositioning of one or more of the interconnected components.

45 Claims, 5 Drawing Sheets

U.S. PATENT DOCUMENTS

| | | | | |
|---|---|---|---|---|
| 4,776,322 A | | 10/1988 | Hough et al. | 128/1.6 |
| 4,800,884 A | | 1/1989 | Heide et al. | 128/419 |
| 4,817,607 A | | 4/1989 | Tatge | 128/419 |
| RE33,170 E | | 2/1990 | Byers | 128/419 |
| 4,904,233 A | | 2/1990 | Hakansson et al. | 600/25 |
| 4,922,333 A | | 5/1990 | Nutting et al. | 358/78 |
| 4,934,368 A | | 6/1990 | Lynch | 128/419 |
| 4,957,478 A | | 9/1990 | Maniglia | 600/25 |
| 4,957,507 A | | 9/1990 | Lenkauskas | 623/10 |
| 4,982,434 A | | 1/1991 | Lenhardt et al. | 381/68.3 |
| 4,998,333 A | | 3/1991 | Skytta | 29/130 |
| 5,012,520 A | | 4/1991 | Steeger | 381/68 |
| 5,015,224 A | | 5/1991 | Maniglia | 600/25 |
| 5,024,224 A | | 6/1991 | Engelbretson | 128/420.6 |
| 5,038,781 A | | 8/1991 | Lynch | 128/419 |
| 5,046,242 A | | 9/1991 | Kuzma | 29/878 |
| 5,085,628 A | | 2/1992 | Engebretson et al. | 600/25 |
| 5,105,811 A | | 4/1992 | Kuzma | 128/420.6 |
| 5,144,952 A | | 9/1992 | Frachet et al. | 128/642 |
| 5,217,011 A | | 6/1993 | Bisch | 128/420.6 |
| 5,220,918 A | | 6/1993 | Heide et al. | 128/420.6 |
| 5,277,694 A | | 1/1994 | Lyesieffer et al. | 600/25 |
| 5,282,858 A | | 2/1994 | Bisch et al. | 623/10 |
| 5,324,311 A | * | 6/1994 | Acken | 607/37 |
| 5,345,509 A | | 9/1994 | Hofer et al. | 381/68.6 |
| 5,358,514 A | | 10/1994 | Schulman et al. | 607/61 |
| 5,370,689 A | | 12/1994 | Causse | 623/10 |
| 5,404,407 A | | 4/1995 | Weiss | 381/68 |
| 5,498,226 A | | 3/1996 | Lenkauskas | 600/25 |
| 5,509,928 A | | 4/1996 | Acken | 607/37 |
| 5,531,787 A | | 7/1996 | Leninski et al. | 623/10 |
| 5,545,219 A | | 8/1996 | Kuzma | 623/10 |
| 5,624,376 A | | 4/1997 | Ball et al. | 600/25 |
| 5,702,342 A | | 12/1997 | Metzler et al. | 600/25 |
| 5,720,631 A | * | 2/1998 | Carson et al. | 439/668 |
| 5,730,628 A | | 3/1998 | Hawkins | 439/843 |
| 5,772,575 A | | 6/1998 | Lesinski et al. | 600/25 |
| 5,782,645 A | | 7/1998 | Stobie et al. | 439/289 |
| 5,788,711 A | | 8/1998 | Lehner et al. | 606/130 |
| 5,795,287 A | | 8/1998 | Ball et al. | 600/25 |
| 5,797,834 A | | 8/1998 | Goode | 600/25 |
| 5,800,336 A | | 9/1998 | Ball et al. | 600/25 |
| 5,814,095 A | | 9/1998 | Muller et al. | 607/57 |
| 5,857,958 A | | 1/1999 | Ball et al. | 600/25 |
| 5,871,514 A | * | 2/1999 | Wiklund et al. | 607/36 |
| 5,871,515 A | * | 2/1999 | Wiklund et al. | 607/36 |
| 5,881,158 A | | 3/1999 | Lesinski et al. | 381/174 |
| 5,913,815 A | | 6/1999 | Ball et al. | 600/25 |
| 5,941,814 A | | 8/1999 | Lehner et al. | 600/25 |
| 5,951,601 A | | 9/1999 | Lesinski et al. | 623/10 |
| 5,984,859 A | | 11/1999 | Lesinski | 600/25 |
| 5,993,376 A | | 11/1999 | Kennedy | 600/25 |
| 6,001,129 A | | 12/1999 | Bushek et al. | 623/10 |
| 6,005,955 A | | 12/1999 | Kroll et al. | 381/328 |
| 6,038,484 A | | 3/2000 | Kuzma | 607/137 |
| 6,039,685 A | | 3/2000 | Bushek | 600/25 |
| 6,174,278 B1 | | 1/2001 | Jaeger et al. | 600/23 |
| 6,176,879 B1 | * | 1/2001 | Reischl et al. | 623/11.11 |

* cited by examiner

CONNECTOR FOR IMPLANTABLE HEARING AID

FIELD OF THE INVENTION

The present invention relates to semi and fully-implantable hearing aid systems, and more particularly, to an interconnection apparatus and method that simplifies implant procedures and facilitates selective removal/replacement of one or more of the implanted components of a hearing aid system.

BACKGROUND OF THE INVENTION

A number of implantable hearing aid devis have been developed for stimulation of the ossicular chain and/or oval window. Such devices can offer superior sound quality and amplification relative to conventional acoustic hearing aids (e.g., devices insertable into the ear canal), while avoiding known shortcomings of acoustic hearing aids (e.g., feedback emissions, etc.).

Known implantable hearing aid devices include those which utilize implanted electromechanical transducers positioned within the middle ear for stimulation of the ossicular chain and/or oval window (see e.g., U.S. Pat. No. 5,702,342), and those which utilize implanted exciter coils to electromagnetically stimulate magnets affixed in the middle ear(see e.g., U.S. Pat. No. 5,897,486). For purposes hereof, such electromechanical transducer and exciter coil magnet arrangements, as well as other implantable middle ear devices capable of stimulating the ossicular chain and/or oval window, will be collectively referred to as "implantable middle ear actuators."

In addition to implantable middle ear actuators, other components of implantable hearing aids systems may be located subcutaneously. By way of example, such additional components may include a receiver for receiving RF signals from an external transmitter and processing electronics to process the received signals and provide an appropriate output signal to an implantable middle ear actuator.

In conjunction with implant procedures, the various implanted components of a given system may entail positioning at a number of differing locations proximal to the mastoid process of a given patient. As will be appreciated, such positioning may require a number of different surgical steps, including for example, the placement of an implantable middle ear actuator through a hole drilled into the mastoid process. Given such positioning requirements, initial component placement can be a challenging procedure and removal/repositioning of selected implanted components of a given implantable hearing aid system (e.g., for reprogramming, replacement, servicing, etc.) may be problematic after the initial implant procedure.

SUMMARY OF THE INVENTION

In view of the foregoing, a primary objective of the present invention is to provide an implantable hearing aid apparatus and method that facilitates the initial positioning of multiple implanted components comprising a given hearing aid system.

An additional objective of the present invention is to provide an implantable hearing aid apparatus and method that facilitates selective replacement/servicing/repositioning of implantable components comprising a given implantable hearing aid system.

Yet a further objective of the present invention is to provide an improved implantable hearing aid apparatus and method that satisfies one or both of the above-noted objectives, while also maintaining the integrity of the operative interconnections made between the different implantable components.

The above-noted objectives and additional advantages may be realized in an inventive apparatus which includes an implantable male connector and an implantable female connector for selectively and slidably receiving the male connector in a recess of the female connector. More particularly, the implantable male and female connectors may each comprise outer housings which may be matably and sealably interconnected, and at least one internal conductor, wherein the respective conductors are selectively interconnected upon adjoinment of the respective outer housings for subcutaneous signal transmission. In this regard, the internal conductor(s) of the male connector and the internal conductor(s) of the female connector may be operably interconnected for signal transmission with separate and different implantable components included in a given implantable hearing aid system. By way of example, such implantable components may be of a type included within an implantable hearing aid component group consisting of: an implantable middle ear actuator, an implantable signal processor, an implantable transcutaneous signal receiver, an implantable microphone and an implantable power source.

In one particular aspect of the invention, at least one pair of the implantable male connector and a first component of the implantable hearing aid component group, and the female connector and a second component of the implantable hearing aid component group, may be non-releaseably interconnected. By way of primary example, said at least one pair may be sealably disposed within a common support structure that serves to define the outer housing of the male or female connector included in the pair. Further in this regard, the support structure may be integrally defined (e.g., via a molding process) and may comprise a biocompatible material selected from a group consisting of:

an elastomeric material (e.g., silicon-based);

an epoxy-resin material; and a ceramic material.

Such materials may be molded about a male or female connector, and one or more implantable hearing aid components, so as to support and insulate such items, while also sealably encapsulating the implantable hearing aid components.

Preferably, the support structure is of a wafer configuration having a predetermined maximum thickness of about 8 mm, and most preferably a predetermined maximum thickness of about 6 mm. Such configuration facilitates subcutaneous placement of the support structure exterior to the skull of a patient, and also serves to minimize any observable protrusion. Further in this regard, it is preferable for the male and female connectors to be oriented for selective interconnection through a side of the wafer-configured support structure (e.g., as opposed to being interconnected through a top or bottom surface of the support structure).

In another specific aspect of the invention, the inventive apparatus may further comprise at least one locking member positionable through the outer housing of the female connector to selectively lock the male connector and female connector in an interconnected relationship. Preferably, when a common support structure is utilized the locking member(s) is disposed for positioning through the side of the support structure (e.g., as opposed to a top or bottom surface of the support structure), so as to contribute to a reduced thickness profile. In this regard, the locking member(s) may be preferably insertable into an opening(s) in the support structure that transversely adjoins the recess of the female connector, wherein the internal conductor(s) of the female connector is also partially disposed within such opening(s).

In an additional aspect of the present invention, the internal conductor(s) of both the female connector and male connector, as well as the locked member(s) if included, may comprise substantially the same conductive metal so as to substantially reduce or avoid any galvanic potential. By way of example, such conductive metal may comprise a metal selected from a group consisting of: titanium, gold, and platinum. Further in this regard, one or more of the components comprising the implantable hearing aid component group optionally employable with the present invention may advantageously comprise or be disposed within a housing comprising a metal selected from the above-noted group.

In yet an additional aspect, the male connector of the inventive apparatus may comprise a central conductor and an outer conductor (e.g., separated by an insulating member therebetween). Further, the female connector may include a conductive first contact member and a conductive second contact member having openings therethrough for slidably receiving the central conductor and outer conductor of the male connector, respectively. To facilitate slidable interconnection between the male connector and female connector, the central conductor and outer conductor of the male connector, as well as the openings in the first and second contact members of the female conductor may be coaxially disposed. In such an arrangement, two locking members may be employed, wherein a first locking member may be disposed through a side opening in the female connector (e.g. aligned side openings through a support structure and the first contact member) to secureably engage the central conductor, and wherein a second locking member may be disposed through a side opening in the female connector (e.g., aligned side openings through a support structure and the second contact member) to secureably engage the outer conductor. In this regard, the first and second locking members may be externally threaded set screws for selective threaded engagement with internally threaded surfaces provided in corresponding side openings of the first and second contact members. First and second separate seal cap members may be provided for insertion into and snap-in engagement with the female connector, thereby sealing the various locking interconnections. The seal cap members may comprise a resilient material and include a central slit that facilitates tool insertion/access therethrough to set screws for selectively "unlocking" of the male connector/female connector (e.g., for component replacement/servicing purposes).

In one embodiment of the present invention an implantable hearing aid apparatus includes an implantable first connector having an outer housing and at least one internal conductor, said at least one internal conductor being operatively interconnected for signal transmission with a middle ear actuator. The apparatus further includes an implantable second connector for selectively and sealably receiving the first connector and having an outer housing and at least one internal conductor. The internal conductor of the second connector is operatively interconnected for signal transmission with an implantable signal processor. Upon selective interconnection of the first connector and second connector, the implantable middle ear actuator and implantable signal processor are operable for subcutaneous signal transmission therebetween.

In the above-described embodiment, the second connector and signal processor may be non-releasably interconnected within a common support structure. Such common support structure may be integrally defined by a molded material, wherein the common support structure has a predetermined maximum thickness of less than about 8 mm for profile reduction purposes. Further, the first connector and second connector may be selectively interconnectable within the support structure through a side surface thereof.

In conjunction with the present invention, an inventive method for use of implantable hearing aid system is also provided. In particular, the inventive method may comprise positioning a first component of an implantable hearing aid system at a first subcutaneous location relative to a patient's skull, wherein the first component is interconnected to a first connector, and the first component is one of an implantable hearing aid component group consisting of: an implantable middle ear actuator; an implantable signal processor; an implantable transcutaneous signal receiver; an implantable microphone; and an implantable power source. The method may further include the step of locating a second component of an implantable hearing aid system at a second subcutaneous location relative to the patient's skull, wherein the second component is interconnected to a second connector that is one of said implantable hearing aid device group. As will be appreciated, the inventive method may also include the step of selectively interconnecting the first and second connectors to establish a sealed, electrical interconnection between corresponding internal conductors disposed within the first and second connectors so as to provide for operative signal transmissions between said first and second implantable components. Of note, to facilitate positioning of the first and second components, the selective interconnection step may preferably be completed after the positioning and/or locating steps (i.e., with the first and/or second components already located in-situ).

The method may further include the step of selectively advancing at least a first locking member through the outer housing of the female connector to secureably interconnect the internal conductors of the first and second connectors. In particular, the first locking member and internal conductor of the female connector may be provided for threading engagement therebetween, wherein the locking member may be rotated into locking engagement with the internal conductor of the male connector.

In a particular application of the method, the first component may comprise an implantable middle ear actuator, wherein the method further includes the step of positioning the implantable middle ear actuator through an opening defined in the mastoid process of a patient's skull. In this regard, such positioning step may provide for contact between a probe end of the middle ear actuator and a middle ear bone or oval window of a patient.

In conjunction with the inventive method, it should be appreciated that the first connector and second connector may be selectively disconnectable, thereby facilitating removal/repositioning of the second component from its corresponding second subcutaneous location while maintaining the first component (e.g., middle ear actuator) at its first subcutaneous location. Such disconnection capability facilitates post implant procedures, including for example reprogramming of an implantable signal processor, servicing of implantable components, etc.

Numerous additional features and advantages of the present invention will become apparent to those skilled in the art upon consideration of the further description that follows.

DETAILED DESCRIPTION

Figure 1:
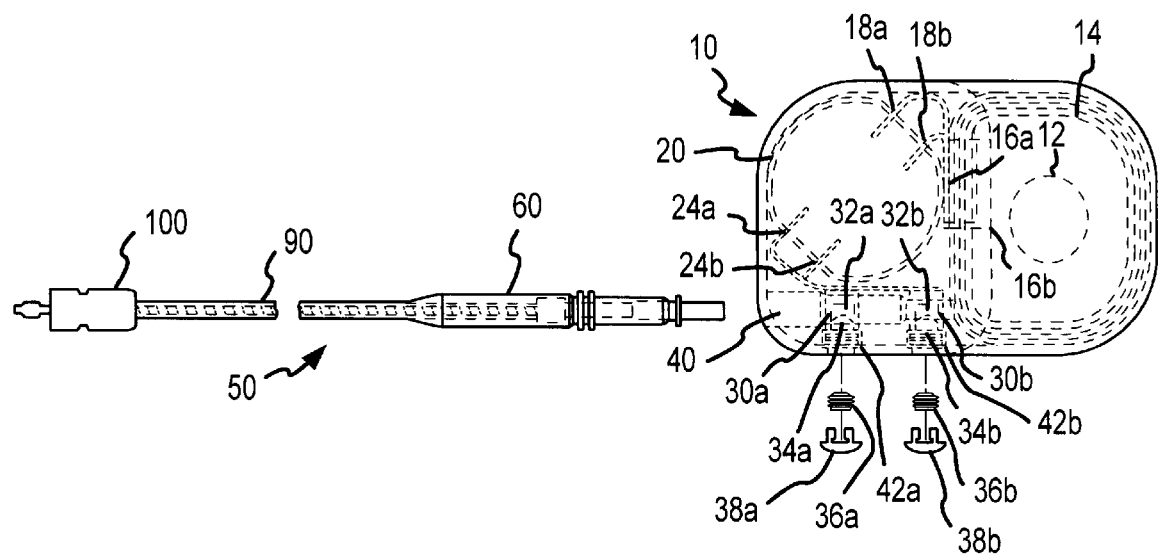
FIG. 1 is an exploded, plan view of one embodiment of the present invention as implemented in a semi-implantable hearing aid system.
Figure 2:
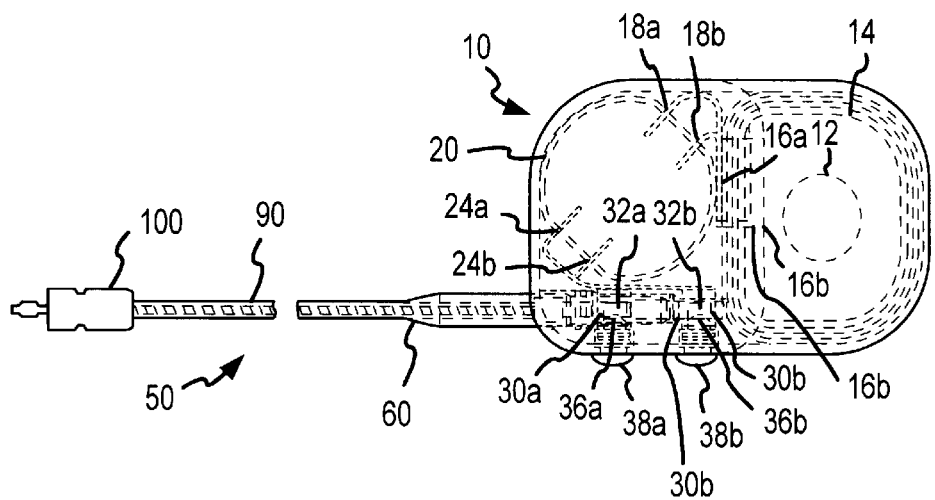
FIG. 2 is a plan, assembly view of the embodiment illustrated in FIG. 1.

FIGS. 1 and 2 illustrate one embodiment of the present invention as implemented in a semi-implantable hearing aid system. The embodiment includes an implantable support structure 10 and a transducer assembly 40. The support structure 10 supports a magnet 12 and an inductive coil 14 electrically interconnected via connection wires at opposite ends 16a and 16b to separate inputs 18a and 18b of a processor unit 20. The support structure 10 further supports first and second electrical contact blocks 30a and 30b which are electrically interconnected via connection wires to separate outputs 24a and 24b of the processor unit 20, respectively (e.g., via welded contacts). Aligned openings 32a and 32b are provided through electrical contact blocks 30a and 30b. Relatedly, an elongated recess 40 is defined in support structure 10, wherein the recess 40 is coaxially aligned with the openings 32a and 32b of the electrical contact blocks 30a and 30b so as to collectively define a female connection port for receiving an elongated male connector 60 provided at a proximal end of a middle ear actuator assembly 50. In the later regard, male connector 60 provides for electrical connection between electrical contact blocks 30a and 30b and a middle ear actuator device 100 disposed at a distal end of a cable line 90 of the actuator assembly 50.

More generally, inductive coil 14 is provided to receive transcutaneous signals (e.g., from an external coil transmitter interconnected to an external signal processor/microphone assembly), and deliver power and acoustic data signals to processor unit 20. In turn, processor unit 20 may generate an output signal that is communicated to the middle ear actuator device 100 via a pair of conductors disposed within the cable line 90, wherein one of the conductive wires is electrically interconnected to electrical contact block 30a and the other conductor is electrically interconnected to the electrical contact block 30b upon insertion of the male connector 60 into the female connector within support structure 10. As may be appreciated, the processor unit 20 output signal is employable by the actuator device 100 to stimulate the ossicular chain and/or oval window of a patient so as to provide for enhanced patient hearing.

As shown in the FIGS. 1 and 2, the embodiment may further comprise first and second locking members 36a and 36b which are selectively positionable through openings 42a and 42b defined through a surface of support structure 10 (e.g., a side surface or top surface thereof). More particularly, locking members 36a and 36b may be externally threaded (e.g., set screws) for threadable engagement with internally threaded surfaces provided in corresponding side openings 34a and 34b provided in contact blocks 30a and 30b. The side openings 34a and 34b adjoin openings 32a and 32b, respectively, wherein upon threadable advancement of the locking members 36a and 36b, a locking interface with male connector 60 (i.e., as inserted in recess 40) may be reliably provided.

In one arrangement, the support structure 10 may be integrally defined in a two step molding process. The first step entails the support of magnet 12, inductive coil 14, processor unit 20, and contact blocks 30a, 30b, in predetermined spatial positions within a mold, with electrical wire connections made therebetween. Additionally, removable plugs are also positioned in the mold to define the desired contours of recess 40 and side openings 42a and 42b. Then a biocompatible, resilient material (e.g., an elastomeric material such as silicon) is introduced into the mold. Alternate materials may also be utilized including epoxy resin or ceramic materials. Upon completion of the first molding step, pins used to support the noted components and plugs may be removed and additional molding material may be flowed into the voids left by the support pins. Thereafter, the plugs defining recess 40 and side openings 42a, 42b may be removed. Preferably, the various noted components and mold are selected to define a support structure 10 having a wafer-shaped configuration and a maximum thickness of about 8 mm, and even more preferably about 6 mm.

The described process provides for sealed encapsulation of the magnet 12, induction coil 14 and processor unit 20. Further, the recess 40 and side openings 42a, 42b are defined so as to facilitate sealable interconnection between the contact blocks 30a, 30b and the male connector 60, as well as sealable locking interconnection between the locking members 36a, 36b, contact blocks 30a, 30b, and male connector 60. In the later regard, sealing caps 38a and 38b may also be utilized for snap-in engagement with contact blocks 30a and 30b, respectively. Sealing caps 38a, 38b may be fabricated from a resilient material and may comprise a central slit therethrough to define a pierceable septum arrangement. Such slit may be utilized for selective insertion of a tool therethrough to unscrew locking members 34a and 34b as may be desired for selective removal of the male connector 60 from recess 40.

Figure 3:
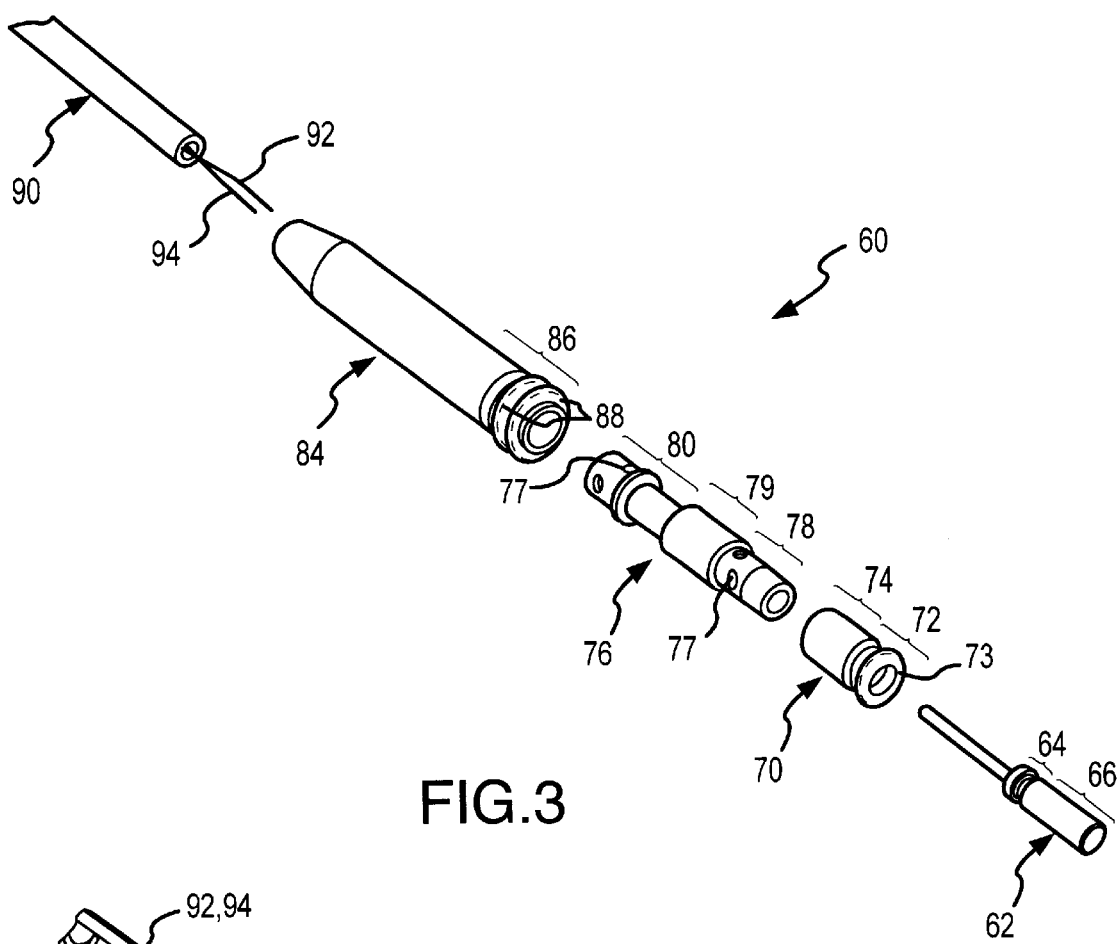
FIG. 3 is an exploded, isometric view of a male connector employable in the embodiment of FIG. 1.
Figure 4:
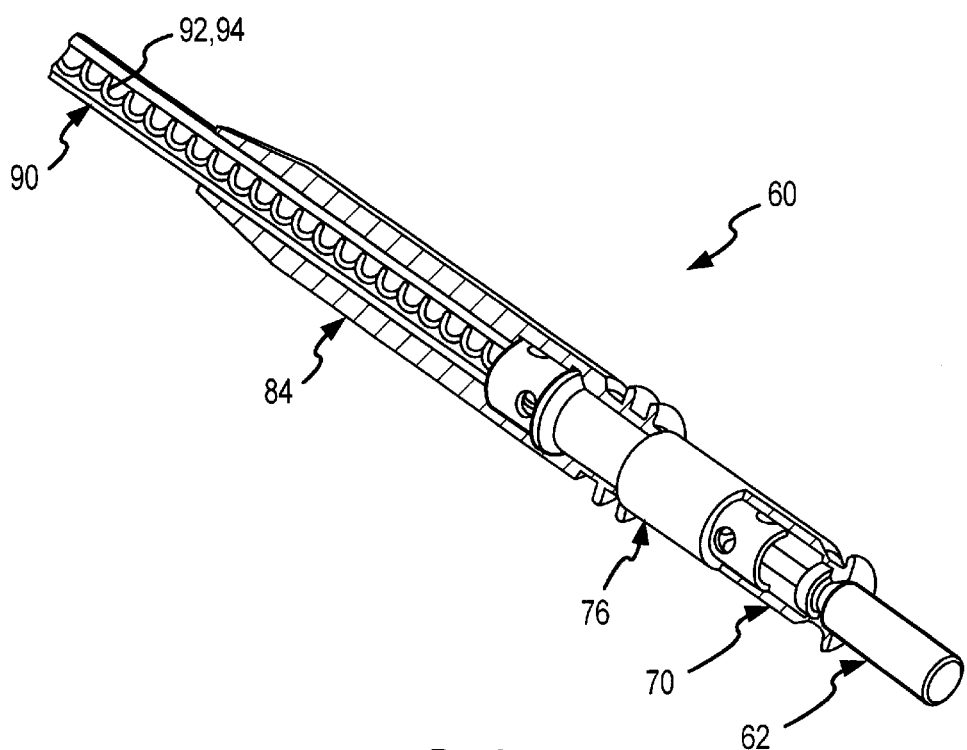
FIG. 4 is a partial cross-sectional, isometric view of the male connector illustrated in FIG. 3.

Referring now to FIGS. 3 and 4, connector 60 will be further described. Connector 60 comprises a solid tip electrode 62, a cylindrical distal seal member 70 having an opening therethrough, a cylindrical ring electrode 76 having an opening therethrough and cylindrical proximal seal member 84 having an opening therethrough. The tip electrode 62 and ring electrode 76 are each constructed from a conductive material (e.g., machined titanium) and are partially, concentrically disposed in the connector 60 for electrical interconnection with first and second conductor wires 92 and 94 of the cable 90, respectively. Wires 92, 94 may be provided in a helical, bifilar arrangement within a resilient, outer insulating sheath into which a moldable material (e.g., a silicon material) has been introduced. Distal seal member 70 and proximal seal member 84 are each also fabricated from a resilient, non-conductive material (e.g., molded silicon). As illustrated, the various components of connector 60 are contoured to facilitate sealable interconnection therebetween.

In particular, tip electrode 62 includes a central exterior portion 64 having a flanged, frusto-conical configuration for snap-in mating engagement with a correspondingly shaped internal surface of an end portion 72 of the distal seal member 70. Another end 74 portion of the distal seal member 70 is sized to slidably receive a distal end portion 78 of the ring electrode 76. Ring electrode 76 further comprises a proximal end 80 having a rimmed-head configuration for conformable, retentive mating engagement with a correspondingly shaped internal surface of an end portion 86 of the proximal seal member 84. Again, such mating engagement facilitates sealable interconnection between the proximal seal member 84 and ring electrode 76. The distal seal member 70 includes an annular ring 73 and the proximal seal member 84 is provided with annular rings 88 to further facilitate sealable interconnection between connector 60 and support structure 10. While not shown in FIG. 4, it is also noted that following assembly of the male connector 60, a flowable insulating material (e.g., a silicon-based material) may be injected into flow ports provided in distal and proximal seal members 76, 84, through one or more ports 77 provided at the distal and proximal ends 78 and 80 of ring electrode 76, and into the internal spaces between the various male connector 60 components described above.

It should also be noted that the contact blocks 30a, 30b, tip electrode 62, ring electrode 76 and locking members 36a, 36b may be fabricated from substantially the same metal to reduce or avoid any galvanic potential therebetween. By way of example, such metal may comprise titanium, gold or platinum. Such materials may also be utilized to house or coat signal processor unit 20 and other implantable components usable in conjunction with the present invention.

Figure 5:
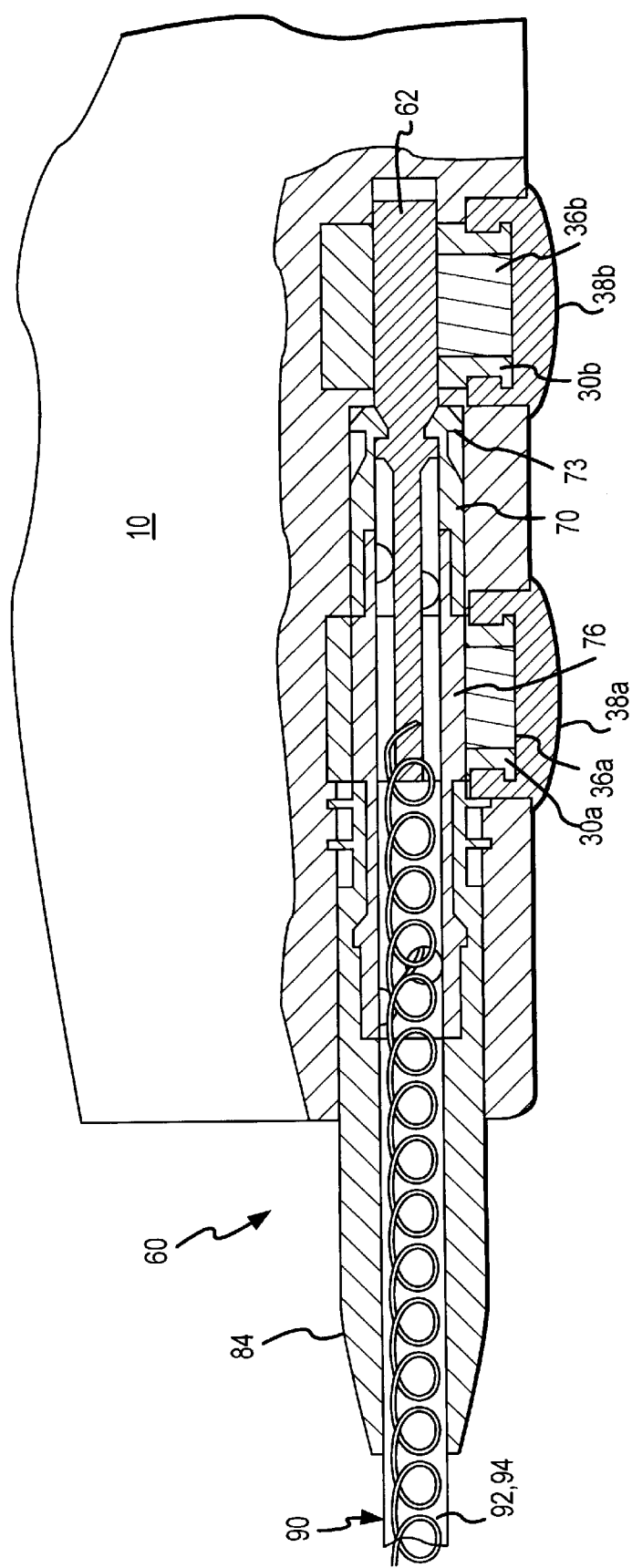
FIG. 5 is a plan, partial cut-away view showing interconnection between the male connector of FIGS. 3 and 4 with a female connector employable in the embodiment of FIGS. 1 and 2.

Reference will now be made to FIG. 5 which illustrates a partial cut away, top view of the male connector 60 as slidably received within electrical contact blocks 30a and 30b and integral support structure 10. As shown in FIG. 5, connector 60 is positioned within recess 40 of the support structure 10. An enlarged end 66 of tip electrode 62 is slidably disposed in the opening 32b of electrical contact block 30b and an enlarged middle portion 79 of ring electrode 76 is slidably received through the opening 32a of the electrical contact block 30a. Further, locking members 36a and 36b have been threadably tightened through side openings 34a and 34b of the electrical contact blocks 30a and 30b, respectively, to securably engage the central enlarged portion 79 of the ring electrode 76 and the enlarged end portion 66 of the tip electrode 62, respectively. For sealing purposes, snap-in sealing caps 38a and 38b have been inserted into the support structure 10 to sealably engage flanges provided at the rims of openings 34a and 34b of the electrical contact blocks 30a and 30b, respectively. To further ensure the establishment of an appropriate sealed interface, annular ring 73 of the resilient distal seal member 70 as well as the annular rings 88 of the proximal seal member 84 sealably engage the internal wall of the recess 40 in the support structure 10.

Figure 6B:
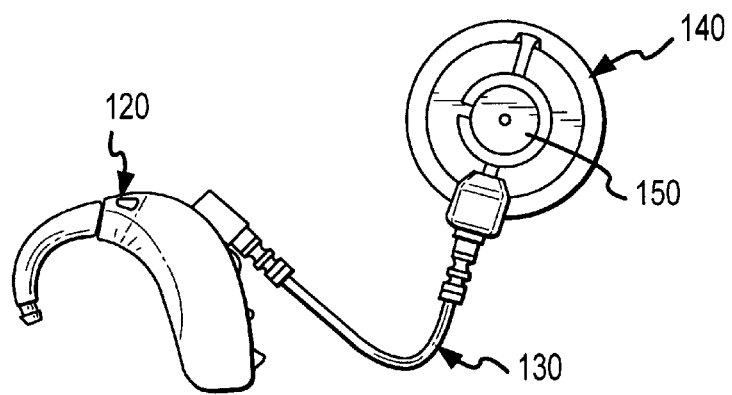
FIG. 6B illustrates external components positionable for use with the internally positionable components shown in FIG. 6A.
Figure 6A:
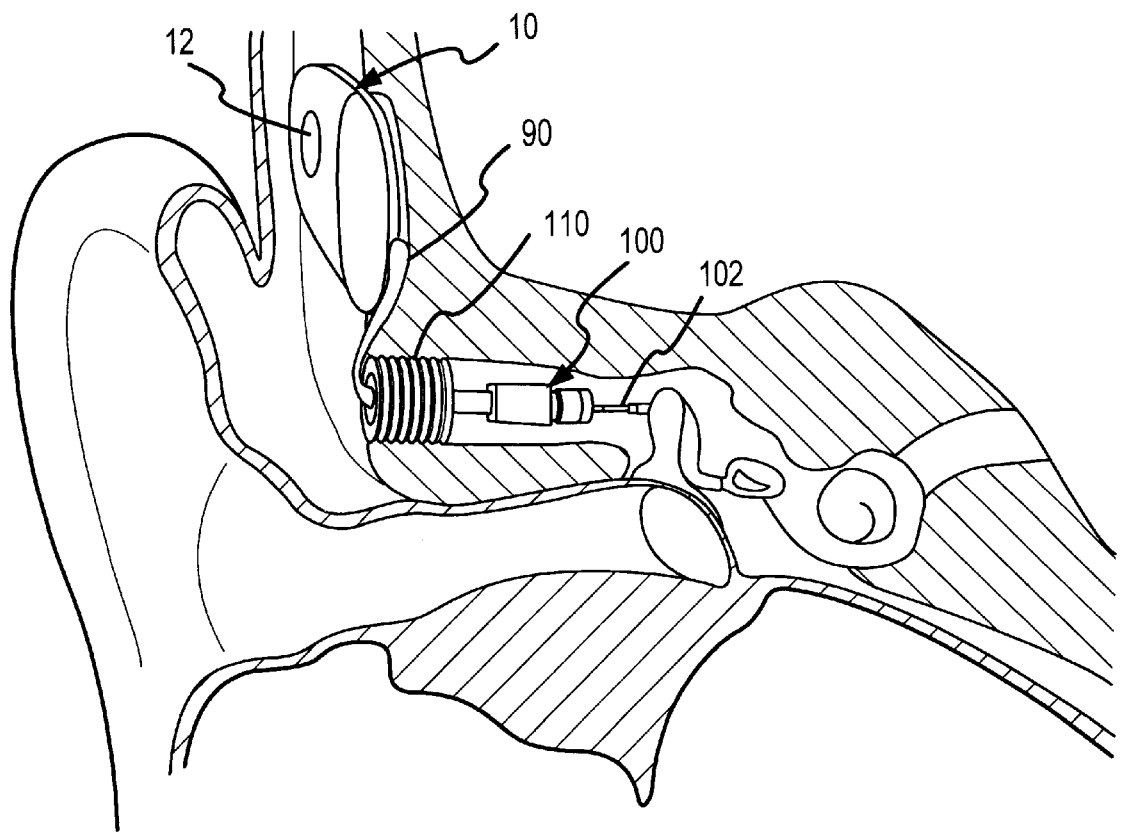
FIG. 6A illustrates positioning of the implantable components of the semi-implantable hearing aid system shown in FIGS. 1 and 2.

As noted above, the embodiment shown in FIGS. 1 and 2 is for use in conjunction with a semi-implantable hearing aid system. FIG. 6A illustrates the positioning of the various implantable components illustrated in FIGS. 1 and 2, while FIG. 6B illustrates external components employable with such an arrangement. In particular, middle ear actuator 100 (e.g., electromechanical transducer) is supportably interconnected to a mounting device 110 threadably disposed within a bored opening in the mastoid process of a patient. A probe end 102 of the middle ear actuator 100 is shown in direct contact with the incus bone for selective stimulation of the ossicular chain. The connector cable 90 is positioned through the mounting device 110, wherein the support structure 10 and components carried thereby may be positioned at a subcutaneous location external to the patient's skull.

As shown in FIG. 6b, the external components may include a behind-the-ear case 120, containing a processor, microphone and battery. Case 120 is interconnected via a short cable 130 to a transmitter coil 140 that is physically interconnected via a webbing arrangement with magnet 150. As will be appreciated, the behind-the-ear case 120 may be supportably positioned over and behind a patient's ear, and magnet 150 may be supportably positioned adjacent to the patient's skull in interfacing relation with the magnet 12 carried by support structure 10. The microphone provided within the behind-the-ear case 120 may receive sound waves to generate a signal that is processed by the processor within case 120. In turn, a processed signal may be transmitted via cable 130 to the transmitter coil 140 for transcutaneous transmission to the induction coil 14 carried by support structure 10.

Figure 7:
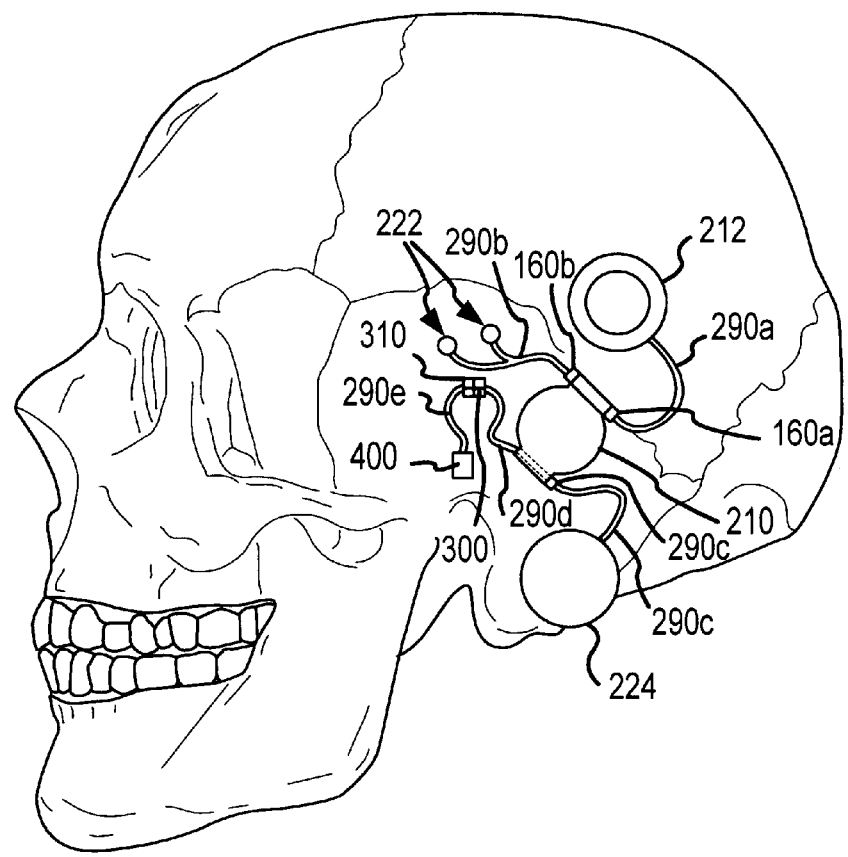
FIG. 7 illustrates the positioning and interconnection of various components in a fully implantable embodiment of the present invention.
Figure 8:
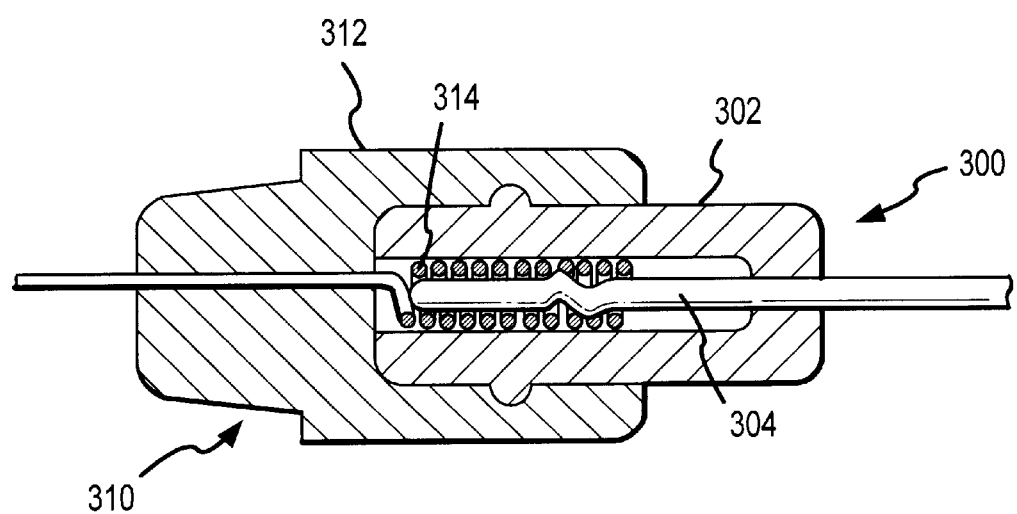
FIG. 8 is a cross-sectional side view of a male connector and female connector employable in conjunction with the embodiment of FIG. 7.

FIGS. 7 and 8 illustrate an alternate embodiment of the present invention as utilized in a fully implantable hearing aid system. As shown in FIG. 7, various components of the system may be separately located at different positions through and adjacent to a patient's skull. In particular, an induction coil 212 (e.g., for transcutaneous signal receiption and/or transmission) may be non-releasably interconnected with a cable line 290a having a connector end 160a provided for selective interconnection with a female connector provided by a support structure 210. Support structure 210 may support a signal processor unit therewithin and may also provide another female connector for selective interconnection with a male connector 160b provided at one end of a cable 290b of a microphone assembly 222. In the later regard, microphone assembly 222 may comprise one or more microphones for receiving sound waves and providing a responsive signal to the processor unit disposed in support structure 210. Support structure 210 may further provide another female connector for selective interconnection with a male connector end 290c provided at one end of a cable 290c. Cable 290c is interconnected to an implantable battery 224 for the provision of power to the processor unit provided in support structure 210. Additionally, support structure 210 may be non-releasably interconnected to a cable line 290d having a first connector end 300 provided at its free end. In turn, first connector end 300 may be selectively interconnectable to a second connector end 310 provided at one end of a cable 290e, wherein the other end of the cable 290e is non-releasably interconnected to a middle ear actuator 400 (e.g., an electromechanical transducer) for stimulation of the middle ear. The connections in the illustrated embodiment may be established utilizing the features described hereinabove.

With particular respect to the connection between the connector ends 300 and 310 described above, FIG. 8 shows one embodiment of a potential interconnection arrangement. More particularly, first connector end 300 is provided with an external housing 302 that is configured for snap-in, sealable engagement with an internal surface defined within an external housing 312 of second connector end 310. Further, first connector end 300 is provided with a central conductor 304 sized for slidable receipt through a coiled end of a central conductor 314 within the second connector end 310, wherein the central conductor 304 may slightly buckle upon interconnection with central conductor 314 to enhance the secure engagement therebetween. As will be appreciated, such an arrangement provides a simple, yet effective mechanism for selective, sealable interconnection between the first and second connectors 300, 310.

The description provided above for purposes of facilitating an understanding of the various features comprising the present invention. Additional embodiments, modifications and extensions will be apparent to those skilled in the art and are intended to be within the scope of the present invention as defined by the claims which follow.

What is claimed is:

1. An implantable hearing aid apparatus comprising:
   an implantable male connector having an outer housing and at least one internal conductor, said male connector being operatively interconnected for signal transmission with a first implantable hearing aid component; and,
   an implantable female connector for selectively and sealably receiving the implantable male connector and having an outer housing and at least one internal conductor, said female connector being operatively interconnected for signal transmission with a second implantable hearing aid component, wherein said implantable male connector and implantable female connector are selectively interconnectable for subcutaneous signal transmission between said first component and said second component;
   wherein at least one pair of said implantable male connector and first component, and said female connector and said second component, are non-releasably interconnected and sealably disposed within a common support structure that is integrally defined.

2. An apparatus as recited in claim 1, wherein said first and second components are different ones of a group consisting of:
   an implantable middle ear actuator;
   an implantable signal processor;
   an implantable transcutaneous signal receiver;
   an implantable microphone; and,
   an implantable power source.

3. An apparatus as recited in claim 1, wherein said common support structure integrally defines said outer housing of said female connector.

4. An apparatus as recited in claim 1, wherein said support structure comprises a bio-compatible material selected from a group consisting of:
   an elastomeric material;
   an epoxy-resin material; and,
   a ceramic material.

5. An apparatus as recited in claim 1, wherein said support structure is of a wafer configuration having a predetermined maximum of about 8 mm.

6. An apparatus as recited in claim 5, wherein said male connector and said female connector are releasably interconnectable through a first side of said support structure.

7. An apparatus as recited in claim 6, further comprising a locking member insertable through an opening in a second side of said support structure to directly engage and selectively lock said male connector and female connector in an interconnected relationship, wherein said second side is adjacent to said first side.

8. An apparatus as recited in claim 1, further comprising:
   at least a first locking member insertable through said outer housing of said female connector to selectively lock said male connector and said female connector in an interconnected relationship.

9. An apparatus as recited in claim 1, said male connector further comprising:
   a central conductor and an outer conductor separated by an insulating layer therebetween; and, said female connector further comprising:
   a first contact member having an opening and a second contact member having an opening for slidably receiving said central conductor and said outer conductor, respectively.

10. An apparatus as recited in claim 9, wherein said central conductor and outer conductor and said male connector and said openings through said first and second contact members are coaxially disposed.

11. An apparatus as recited in claim 1, wherein said at least one internal conductor of said female connector and said at least one internal conductor of said male connector comprise substantially the same conductive metal.

12. An implantable hearing aid apparatus comprising:
    an implantable first connector having an outer housing and at least one internal conductor, said at least one internal conductor of the first connector being operatively interconnected for signal transmission with an implantable middle ear actuator; and,
    an implantable second connector for selectively and sealably receiving the implantable first connector and having an outer housing and at least one internal conductor, said at least one internal conductor of the second connector being operatively interconnected for signal transmission with an implantable signal processor, wherein the second connector and the signal processor are non-releasably interconnected within a common support structure that is integrally defined, and wherein the implantable first connector and implantable second connector are selectively interconnectable for subcutaneous signal transmission between said implantable signal processor and said implantable middle ear actuator.

13. An apparatus as recited in claim 12, wherein said common support structure comprises a bio-compatible material selected from a group consisting of:
    an elastomeric material;
    an epoxy-resin material; and,
    a ceramic material.

14. An apparatus as recited in claim 13, wherein said common support structure is integrally defined by a molded material, and wherein said common support structure has a predetermined maximum thickness of about 8 mm.

15. An apparatus as recited in claim 13, wherein said first connector and second connector are selectively interconnectable within said support structure through a side thereof.

16. An apparatus as recited in claim 12, said male connector further comprising:
    a central conductor and an outer conductor separated by an insulating layer therebetween; and, said female connector further comprising:
    a first contact member having an opening and a second contact member having an opening for slidably receiving said central conductor and outer conductor, respectively.

17. A method for use within an implantable hearing aid system comprising:
    positioning a first component of an implantable hearing aid system at a first subcutaneous location relative to a patient's skull, wherein said first component is interconnected to a first connector;
    locating a second component of said implantable hearing aid system at a second subcutaneous location relative to said patient's skull, wherein second component is interconnected to a second connector;

interconnecting said first connector and said second connector to establish a sealed, electrical interconnection between corresponding internal conductors thereof for subcutaneous signal transmission between said first and second components; and, selectively advancing at least a first locking member through an opening in an outer housing of said first connector to directly engage the second connector and thereby lock said first connector and second connector in an interconnected relationship.

18. A method as recited in claim 17, wherein said first component and said second component are different ones of a group consisting of:

an implantable middle ear actuator;
an implantable signal processor;
an implantable transcutaneous signal receiver;
an implantable microphone; and,
an implantable power source.

19. A method as recited in claim 17, wherein said interconnecting step is completed in-situ after said positioning and locating steps.

20. A method as recited in claim 17, wherein said first connector and said second connector are selectively disconnectable for removal of said second component from said second subcutaneous location and maintenance of said first component at said first subcutaneous location relative to said patient's skull.

21. An implantable hearing aid apparatus comprising:

an implantable male connector having an outer housing and at least one internal conductor, said male connector being operatively interconnected for signal transmission with a first implantable hearing aid component;

an implantable female connector for selectively and sealably receiving the implantable male connector and having an outer housing and at least one internal conductor, said female connector being operatively interconnected for signal transmission with a second implantable hearing aid component, wherein said female connector and said second implantable hearing aid component are sealably disposed within a common support structure that integrally defines said outer housing of said female connector, and wherein said implantable male connector and implantable female connector are selectively interconnectable for said subcutaneous signal transmission between said first component implantable hearing aid component and said second implantable hearing aid component; and, a first locking member selectively insertable through a first opening of said outer housing of said female connector to directly engage said male connector and thereby lock said male connector and said female connector in an interconnected relationship.

22. An apparatus as recited in claim 21, wherein said male connector and female connector are releasably interconnectable through a first side of said common support structure, and wherein said first opening is located on a second side of said support structure which is adjacent to said first side.

23. An apparatus as recited in claim 21, wherein said support structure comprises a biocompatible material selected from a group consisting of:

an elastomeric material;
an epoxy-resin material; and,
a ceramic material.

24. An apparatus as recited in claim 21, wherein said first locking member is selectively positionable for direct engagement with said at least one internal conductor of the male connector.

25. An apparatus as recited in claim 24, wherein said internal conductor of said female connector directly engages said first locking member when said first locking member is positioned through said first opening.

26. An apparatus as recited in claim 25, wherein a portion of said at least one internal conductor of said female connector is disposed within said opening.

27. An apparatus as recited in claim 26, wherein said portion of said at least one internal conductor of said female connector is threaded for receipt of a threaded portion of said first locking member.

28. An apparatus as recited in claim 25, wherein said first locking member is electrically conductive.

29. An apparatus as recited in claim 28, wherein said locking member and said at least one internal conductor of said female connector and male connector each comprise substantially the same conductive material.

30. An apparatus as recited in claim 29, wherein said second implantable hearing aid component is housed within a housing having an outer surface comprising substantially said same conductive material.

31. An apparatus as recited in claim 30, wherein said same conductive metal is selected from a group consisting of:

titanium;
gold; and,
platinum.

32. An apparatus as recited in claim 24, further comprising:

a second locking member selectively insertable through a second opening of said outer housing of said female connector to directly engage another internal conductor of said male connector.

33. An apparatus as recited in claim 32, wherein another internal conductor of said female connector directly engages said second locking member when said second locking member is positioned through said second opening.

34. An implantable hearing aid apparatus comprising:

an implantable male connector having an outer housing, a central conductor and an outer conductor, said male connector being operatively interconnected for signal transmission with a first implantable hearing aid component; and, an implantable female connector for selectively and sealably receiving the implantable male connector, and including an outer housing and first and second conductive members each having openings for slidably receiving said central conductor and said outer conductor of said male conductor, respectively, said female connector being operatively interconnected for signal transmission with a second implantable hearing aid component, wherein said female connector and said second implantable hearing aid component are sealably disposed within a common support structure that integrally defines said outer housing of said female connector, and wherein said implantable male connector and implantable female connector are selectively interconnectable for said subcutaneous signal transmission between said first component implantable hearing aid component and said second implantable hearing aid component.

35. An apparatus as recited in claim 34, further comprising:

a second locking member selectively insertable in a second opening in said outer housing of said female connector to directly engage said male connector and thereby lock said male connector and said female connector in an interconnected relationship.

36. An apparatus as recited in claim 35, wherein said first and second locking members are disposed for selective direct engagement which said central conductor and outer conductor of said male connector, respectively.

37. An apparatus as recited in claim 36, wherein portions of said first and second conductive members of said female connector are disposed within said first and second openings, respectively.

38. An apparatus as recited in claim 37, wherein said portions of said first and second conductive members of said female connector are threaded for receipt of corresponding threaded portions of said first and second locking members, respectively.

39. An apparatus as recited in claim 36, wherein said first and second locking members are electrically conductive.

40. An apparatus as recited in claim 39, wherein said first and second locking members and said first and second conductive members of said female connector comprise substantially the same conductive material.

41. An apparatus as recited in claim 40, wherein said substantially same conductive metal is selected from a group consisting of:
   titanium;
   gold; and,
   platinum.

42. A method as recited in claim 17, further comprising:
   placing a sealing cap in said opening in said outer housing of said first connector to substantially block fluid external to the implantable hearing aid system from entering said opening so as to protect said first locking member.

43. An apparatus as recited in claim 21, further comprising:
   a sealing cap selectively insertable in said opening in said outer housing of said female connector to substantially block fluid external to the apparatus from entering said opening so as to protect said first locking member.

44. An apparatus as recited in claim 34, wherein said male connector and said female connector are releasably interconnectable through a first side of said common support structure, and wherein said first and second openings are located on a second side of said support structure which is adjacent to said first side.

45. An apparatus as recited in claim 34, wherein said support structure comprises a biocompatible material selected from a group consisting of:
   an elastomeric material;
   an epoxy-resin material; and,
   a ceramic material.

* * * * *